(12) United States Patent
Dinkelborg et al.

(10) Patent No.: US 6,855,103 B2
(45) Date of Patent: Feb. 15, 2005

(54) RADIOACTIVE IMPLANTABLE DEVICES AND METHODS AND APPARATUSES FOR THEIR PRODUCTION AND USE

(75) Inventors: Ludger Dinkelborg, Berlin (DE); Klaus Urich, Berlin (DE)

(73) Assignee: Schering AG, Berlin-Wedding (DE)

(*) Notice: Subject to any disclaimer, the term of this patent is extended or adjusted under 35 U.S.C. 154(b) by 158 days.

(21) Appl. No.: 10/217,379

(22) Filed: Aug. 13, 2002

(65) Prior Publication Data

US 2003/0065242 A1 Apr. 3, 2003

Related U.S. Application Data

(60) Provisional application No. 60/312,029, filed on Aug. 13, 2001.

(51) Int. Cl.[7] ............................. A61N 5/00; C25D 5/10
(52) U.S. Cl. .......................................... 600/3; 205/170
(58) Field of Search ............................. 627/2.24, 2.28, 627/2.3, 407.1, 414, 417, 418, 6; 600/3; 425/5; 428/655, 654; 205/170, 181; 106/1.12, 1.13, 1.15, 1.18, 1.21, 1.27

(56) References Cited

U.S. PATENT DOCUMENTS

| | | | | |
|---|---|---|---|---|
| 6,059,714 | A | * 5/2000 | Armini et al. ................. | 600/3 |
| 6,077,413 | A | 6/2000 | Hafeli et al. | |
| 6,394,945 | B1 | * 5/2002 | Chan et al. ..................... | 600/3 |
| 6,475,644 | B1 | * 11/2002 | Hampikian et al. ......... | 428/655 |
| 6,503,640 | B2 | * 1/2003 | Wittebrood et al. ........ | 428/654 |
| 6,709,693 | B1 | * 3/2004 | Dinkelborg et al. ....... | 427/2.24 |
| 2003/0204125 | A1 | * 10/2003 | Brauckman et al. ........... | 600/3 |

FOREIGN PATENT DOCUMENTS

| WO | WO 98/48851 | 11/1998 |
|---|---|---|
| WO | WO 00/29501 | 5/2000 |

OTHER PUBLICATIONS

"Edge Restenosis After Implantation of High Activity 32P Radioactive B–Emitting Stents"; Remo Albiero, MD, et al.; Emodianamica Centro Cuore Columbus, Milan, Italy; 2000 American Heart Association, Inc.

"Electrodeposition of radioactive rhenium onto stents to prevent restenosis"; U. O. Hafeli et al., Biomaterials 19, 1998, 925–933.

International Search Report for Counterpart PCT Application No.: PCT/US02/205709.

* cited by examiner

*Primary Examiner*—Samuel G. Gilbert
*Assistant Examiner*—Nikita R. Veniaminov
(74) *Attorney, Agent, or Firm*—Millen, White, Zelano & Branigan, P.C.

(57) ABSTRACT

A radiolabeled implantable device includes a base, a first layer including Cu and a radioactive isotope on the base, and a second layer including Sn on the first layer. Preferably, the base is formed of stainless steel and the radioactive isotope is a radioisotope of Re, such as $^{188}$Re or $^{186}$Re. Alternately, radioisotopes of the following elements may be used: Be, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Te, Hf, Ta, W, Os, Ir, Pt, Au, Hg, Tl, Pb, Bi, Po, At, Th, Pa, U, Np, Pu, Am, Cm, Bk, Cf, Es, Fm, Md, No, Lr. In addition, a process for producing a radiolabeled implantable device includes depositing a first layer including Cu and a radioactive isotope on a base, and depositing a second layer including Sn on the first layer. The process may further include removing $Cr_2O_3$ from the base and/or rinsing the base prior to depositing the first layer thereon.

51 Claims, 4 Drawing Sheets

RADIOACTIVE IMPLANTABLE DEVICES AND METHODS AND APPARATUSES FOR THEIR PRODUCTION AND USE

CROSS REFERENCE TO RELATED APPLICATION

This application claims the benefit of U.S. Provisional Application Ser. No. 60/312,029, filed on Aug. 13, 2001, the contents of which are incorporated herein by reference.

BACKGROUND OF THE INVENTION

The present invention relates generally to radiolabeled implantable devices and, more particularly, to radiolabeled stents for reducing restenosis, and methods and apparatuses for their production and use.

Vessel stenosis in humans and animals can occur, for example, by obstruction of the vessels (e.g., arteriosclerosis) or by external pressure (e.g., tumors) being applied on the vessels. After stenotic sites are treated (e.g., by balloon angioplasty) to clear or enlarge the obstructed or constricted vessels, stents are often placed within the vessel to prevent restenosis (the re-occlusion of vessels). Nevertheless, restenosis still occurs in a significant number of patients.

While the cause of restenosis is not clearly understood, it is believed that proliferation of smooth muscle cells in the treated vessels results in scar tissue formation, which can eventually lead to blood flow restriction or blockage in the vessels. Because local irradiation has been shown to reduce the growth of smooth muscle cells, one approach to prevent restenosis is to locally irradiate the stenotic site after stent deployment. Another approach, as disclosed in U.S. Pat. No. 5,059,166 to Fischell et al. ("the '166 patent"), is to implant a radioactive stent in the treated vessel to inhibit smooth muscle cell growth and thereby prevent restenosis.

As discussed in "Electrodeposition of Radioactive Rhenium onto Stents to Prevent Restenosis," by Urs O. Häfeli et al., *Biomaterials*, Vol. 19, pgs. 925–933 (1998) ("Biomaterials"), radioactive stents currently need to be produced and activated in advance of implantation, and therefore cannot be tailored—by stent length and type or by radioactivity level—for individual lesion characteristics. Biomaterials suggests an approach whereby radioactive stents can be produced in 15 minutes, just prior to implantation. In Biomaterials, radioactive stents are produced by coating conventional stainless steel or tantalum stents with radioactive rhenium. The conventional stent is placed in a series of rinsing and electroplating solutions, one of which contains radioactive rhenium ($^{186}$Re or $^{188}$Re or both). The plated stent contains radioactive rhenium in a 1.2 µm-thick cobalt layer, with an outer 2 µm-thick layer of gold. According to Biomaterials, the gold layer provides the radioactive stent with excellent chemical stability, good bending and biocompatibility properties, and improved visibility during fluoroscopy.

While Biomaterials appears to have made significant strides in the production of radioactive stents, a number of improvements relating to radioactive stents and their production and use in clinical environments are desirable. For example, recent studies (e.g., "Edge Restenosis after Implantation of High Activity P-32 Radioactive Beta-Emitting Stents," Albiero et al., Circulation 2000, 101:2454–2457) indicate that restenosis can and does occur at the ends of radioactive stents implanted in treated vessels. A current theory attributes the cause of this "candy wrapper" restenosis to the radioactivity level of the radioactive stent. If the radiation dosage is too low or too short in duration, smooth muscle cell growth occurs and eventually the vessel wall at the ends of the stent constricts or closes. On the other hand, if the radiation dose is too high or too long in duration, the tissue behind the smooth muscle cells constricts in reaction to the radiation, thereby constricting or closing the vessel by external pressure. Thus, a need exists for a radioactive stent that delivers an optimal amount of radiation to a stenotic site to prevent restenosis.

In addition, a need exists for an electrochemical deposition technique whereby radioactive stents and other implantable devices are easily and safely produced with little or no intervention by hospital or technical personnel. For example, it is desirable to provide an electrochemical deposition technique that requires a limited number of electrolytic cells and/or solutions to produce a radioactive implantable device, such as a stent.

Furthermore, improved techniques for preparing implantable devices for radiolabeling, for optimizing the surface finish of radioactive implantable devices and for customizing and adjusting the radioactivity level of radioactive implantable devices are desirable.

SUMMARY OF THE INVENTION

The present invention provides radiolabeled implantable devices, such as stents, wires and seeds, and methods and apparatuses for their production and use.

The present invention also provides a number of improvements to and improved techniques for producing and using conventional radiolabeled implantable devices, including, but not limited to, those discussed above. For example, the radiolabeled implantable devices of the present invention may be customized for optimal delivery of radiation to a desired site. Further, the radioactivity level of a radiolabeled implantable device may be adjusted or corrected without having to discard the implantable device. In addition, the present invention provides improved techniques for radiolabeling implantable devices by electrochemical deposition and for optimizing the surface finish thereof. Moreover, the present invention provides improved techniques for preparing implantable devices for radiolabeling.

In one aspect, the present invention provides a radiolabeled implantable device including a base, a first layer including Cu and a radioactive isotope on the base, and a second layer including Sn on the first layer. Preferably, the base is formed of stainless steel and the radioactive isotope is a radioisotope of Re, such as $^{188}$Re or $^{186}$Re. Alternately, radioisotopes of the following elements may be used: Be, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Te, Hf, Ta, W, Os, Ir, Pt, Au, Hg, Tl, Pb, Bi, Po, At, Th, Pa, U, Np, Pu, Am, Cm, Bk, Cf, Es, Fm, Md, No and Lr.

In another aspect, the present invention provides a process for producing a radiolabeled implantable device. The process includes depositing a first layer including Cu and a radioactive isotope on a base, and depositing a second layer including Sn on the first layer. Preferably, the base is formed of stainless steel and the radioactive isotope is a radioisotope of Re, such as $^{188}$Re or $^{186}$Re. The process may further include removing $Cr_2O_3$ from the base prior to depositing the first layer thereon and/or rinsing the base prior to depositing the first layer thereon.

Preferably, the first layer is deposited on the base and/or the second layer is deposited on the first layer by electrochemical deposition. Further, the current level and/or duration of the electrochemical deposition may be adjusted to customize the radioactivity level of the implantable device and/or to compensate for the radioactive decay of the radiolabeling solution. In addition, the electrical current direction of the electrochemical deposition may be reversed or switched for a period of time to optimize the surface finish preparation of the implantable device by electropolishing.

In yet another aspect of the present invention, a process for producing a radiolabeled implantable device includes depositing a layer comprising Cu, Sn and a radioactive isotope on a base. Preferably, the base is formed of stainless steel and the radioactive isotope is a radioisotope of Re, such as $^{188}$Re or $^{186}$Re.

In still another aspect, the present invention provides a process of preparing a stainless steel implantable device for radiolabeling. The process includes removing $Cr_2O_3$ from the implantable device prior to radiolabeling. The $Cr_2O_3$ may be removed by electroetching the implantable device or by immersing the implantable device in an acid solution. Preferably, the $Cr_2O_3$ removal process continues until an electropolishing voltage drop is noticed.

In yet still another aspect, the present invention provides a process of optimizing the surface finish of a radiolabeled implantable device. The process preferably includes reducing the current level and/or switching the current direction to electropolishing mode for a period of time during an electrochemical deposition. The process may further include adjusting the duration of the electrochemical deposition.

In a further aspect, the present invention provides a process of adjusting the radioactivity of a radiolabeled implantable device. Preferably, the process includes rinsing the implantable device to remove a desired amount of radioactivity therefrom. The process may include immersing the implantable device in ethanol or water.

In still another aspect, the present invention provides a process of customizing a radiolabeled implantable device produced by electrochemical deposition of a radioactive isotope on the implantable device. Preferably, the process includes compensating for the radioactive decay of the radioactive isotope by plating conditions, especially adjusting the duration and/or current level of the electrochemical deposition.

In yet a further aspect, the present invention provides a process of customizing the radioactivity of a radiolabeled implantable device produced by electrochemical deposition. Preferably, the process includes adjusting the configuration of the anode to vary the deposition of the radioactive isotope on the implantable device. The configuration of the anode may be adjusted by varying the length of the anode and/or by substantially disposing the anode around the circumference of the implantable device. In addition, the anode may be formed in a plurality of turns, such as a spring, and the density or "tightness" of the turns may be varied in certain sections of the anode to in turn vary the mount of radioactivity deposited on corresponding sections of the implantable device.

The present invention, along with the attributes and attendant advantages thereof, will best be appreciated and understood in view of the following detailed description taken in conjunction with the accompanying drawings.

DETAILED DESCRIPTION OF THE PREFERRED EMBODIMENTS OF THE INVENTION

Figure 1:
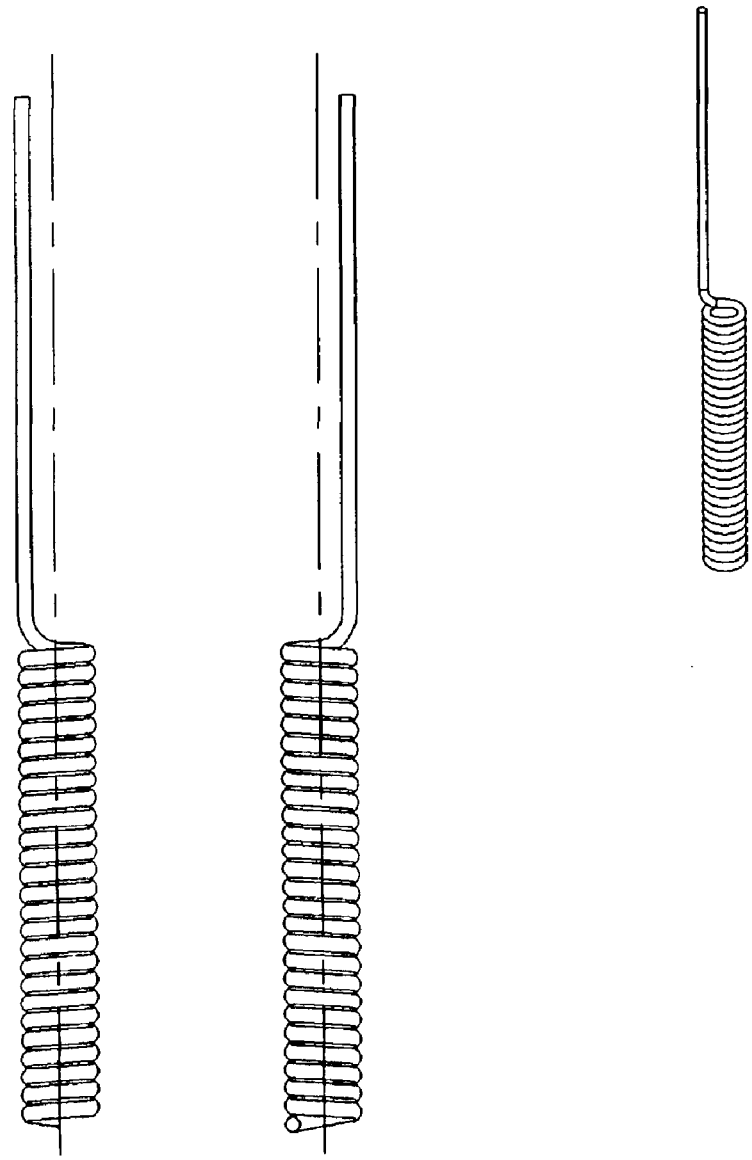
FIG. 1 illustrates various views of an anode utilized in the plating cell of the preferred embodiment of the present invention.

The present invention is broadly applicable to radiolabeled implantable devices, including stents, wires and seeds. However, for illustrative purposes only, the present invention is primarily described in the examples below in terms of radiolabeled stents and, in particular, Jomed coronary wave-configuration stents radiolabeled with $^{188}$Re.

In a preferred embodiment of the present invention, an implantable device is radiolabeled by electrochemically depositing a first layer of Cu and a radioactive isotope of Re on a stainless steel implantable device, and then electrochemically depositing a second layer of Sn on the first layer to seal the radiolabeled implantable device. As discussed above, suitable implantable devices include, but are not limited to, stents, wires and seeds.

According to the preferred embodiment of the present invention, the electrochemical process that produces the radiolabeled implantable device is represented by the following chemical reactions:

Anodic Etch

During the anodic cycle, the electrochemical reactions are believed to be (where Cu(o) is metallic copper):

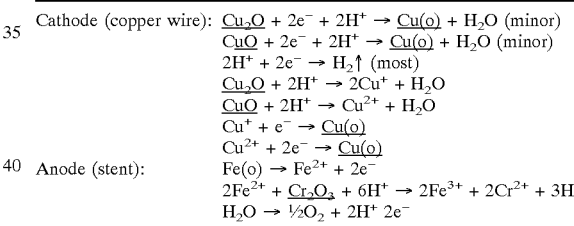

Radiolabeled Strike (with Re-188)

The polarity is reversed such that the stent becomes the cathode (negatively charged) and the copper wire becomes the anode (positively charged).

Cathode (stent) reactions at early time: The main cathodic labeling chemical reactions are believed to be:

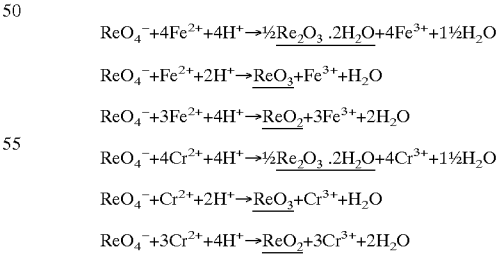

A small amount of reduction by adsorbed hydrogen, perhaps at catalytic nickel sites on the depassivated stent, may also contribute to the reduction of Re(VII) as follows:

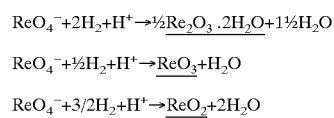

where the hydrogen is produced locally adsorbed on the surface of the cathode/stent as follows:

$$2H^+ + 2e^- \rightarrow H_2 \uparrow$$

Later in the labeling step, more cathodic reactions occur which produce soluble copper that seals the insoluble Re oxides onto the surface of the stent:
Anodic (copper wire) reactions:

$$2Cu(o) + H_2O \rightarrow Cu_2O + 2H^+ + 2e^-$$

$$Cu_2O + H_2O \rightarrow 2CuO + 2H^+ + 2e^-$$

$$Cu_2O + 2H^+ \rightarrow 2Cu^+ + H_2O$$

$$CuO + 2H^+ \rightarrow Cu^{2+} + H_2O$$

Hence small amounts of copper ion are believed to enter the electrolyte by anodic etch during the labeling step. This transformation to oxides of copper, especially to cuprous oxide ($Cu_2O$) is visually apparent within seconds of switching the potential. The reactions are believed to be:

Cathode (stent) reactions at later time:

$$Cu^{2+} + 2e^- \rightarrow Cu(o)$$

$$2Cu^{2+} + 2e^- + H_2O \rightarrow Cu_2O + 2H^+$$

$$Cu^+ + e^- \rightarrow Cu(o)$$

The brick red color of the stent after striking suggest that the major reaction involving copper deposition at the stent cathode is formation of cuprous oxide, $Cu_2O$, probably an alloy with copper metal, and with essentially no cupric oxide copper present due to the low acidity, color, and ease of reduction of CuO.

Rinse

An ethanol rinse is used to remove acid (HCl) and water from the stent. However, the metal ions are not soluble, or not sufficiently quickly soluble, in the ethanol so that they remain behind at the surface of the stent (provided excessive rinsing is not used). Without the acid present, the cationic trivalent metal ions readily precipitate. The reactions are believed to be:

$$Fe^{3+} + 3H_2O \rightarrow Fe(OH)_3 + 3H^+$$

$$Cr^{3+} + 3H_2O \rightarrow Cr(OH)_3 + 3H^+$$

where the $H^+$ is present as HCl and is therefore easily rinsed away by the ethanol.

The Fe and Cr hydroxides are known to be excellent scavengers of metal ions during precipitation, and may therefore be expected to assist holding the hydrated Re oxides to the surface of the stent.

The following examples are provided for illustrative purposes, and are directed to the most preferred embodiment of the present invention directed to stents that are radiolabeled with a radioactive isotope of Re.

EXAMPLE 1

Radiolabeling a Stent or Other Implantable Device

A. Determining the Amount of Activity to Add to the Label Bath

The following procedure is used to calculate the volume of radioactive solution that must be transferred to the strike bath to obtain a desired radioactivity level on the stent at the time of implantation.

A requirement for this procedure is a source of radioactivity with a known (measured) activity level at the time it is obtained. Liquid is withdrawn from this source by pipettor and transferred to the strike solution as stent radiolabeling procedures are performed.

Three inputs to the procedure are:

Final desired activity of the stent to be implanted—$S_0$ (MBq)

Initial specific activity of the eluent—a (MBq/mL)

Length of the 1.8 mm diameter stent—L (mm)

Three system efficiencies are inputs to the procedure and have been experimentally determined (See Table 1 below) for the Jomed coronary wave-configuration stents.

Label efficiency—$E_1$ (activity transferred to stent during strike)

Process—$E_p$ (activity lost from stent during tin plate and rinses)

Expansion—$E_e$ (activity lost during expansion)

Step 1: Calculate S, the activity desired on the stent at the end of the radiolabeling process. This allows for decay time between radiolabeling and implantation.

$$S = \frac{S_o}{E_e * \exp(-k * t_2)}$$

Where:

S=activity of stent after labeling process (MBq)

$S_0$=required activity of stent upon implantation (with expansion)

$t_2$=time between label and implantation (hours)

$E_e$=expansion efficiency=1

$$k = \ln(2)/t_{1/2}$$

Where $t_{1/2}$=16.94 hours for $^{188}Re$

Step 2: Calculate $A_0$, the activity required in the label solution (strike bath) at the time the stent is radiolabeled.

$$A_0 = \frac{S}{E_l * E_p}$$

Where:

$A_0$ required activity (MBq) of label solution at time of label creation

S=required activity (MBq) of stent after label $E_1$=label efficiency $E_p$=process efficiency=0.817

Where label efficiency $E_1$ is a calculated using the stent length, L (mm)

$$E_1 \, 0.0027*L + 0.048$$

TABLE 1

Experimental Efficiencies for Electroplate Labeling of $^{188}Re$

| Jomed Wave-Configuration Stent | Coronary (1.8 mm diameter) |
|---|---|
| Label efficiency | 0.0027*L + 0.048 |
| Process efficiency | 0.841 |
| Expansion efficiency | 1.0 |

Step 3: Calculate V, the volume of liquid (mL) to be transferred from the $$V = \frac{A_o}{a * \exp(-k * t_1)}$$

radioisotope source to the label solution (strike bath)
Where:
  k=1n(2)/$t_{1/2}$ (where $t_{1/2}$=16.94 hours for $^{188}$Re)
  $t_1$=hours from eluent activity measurement to label solution creation
  a=specific activity (MBq/mL) of label at eluent measurement time
  $A_0$=required activity (MBq) of label solution at time of label creation
  V=volume (mL) of eluent to add to label solution to get activity $A_0$ B. Prepare $^{188}$Re Label Solution (Strike Electrolyte)

Transfer the calculated volume of Rhenium eluent (bolus) needed to provide the necessary activity level on the stent, corrected for deposition yield. Add an equal volume of 2.0N HCl. Add 1.0N HCl up to the volume indicated in Table 2. The total liquid volume is selected so that the stent is barely submerged during the labeling operation.

Crimp cap the vial, mix thoroughly, and measure the total activity of the vial.

Adjust or remake the strike solution if the needed activity is not achieved.

TABLE 2

Process Solution Volume Table

| Stent Length (mm) | Solution Volume (µL) |
|---|---|
| 9, 12 | 750 |
| 15, 16 | 1000 |
| 19, 20 | 1200 |
| 26 | 1500 |
| 30, 32 | 1700 |
| 40 | 2000 |
| 50 | 2400 |
| 60 | 2800 |

In a preferred embodiment, the anodes are coiled wire. Turns of the coil should be evenly spaced with a gap of approximately 1.6 mm between turns. Anodes should be inspected and adjusted before being placed into a cell. The volumes in Table 2 may not cover the stent correctly if the anode coil turns are not spaced evenly. Please refer to FIG. 1 for a drawing of a suitable anode configuration.

C. Insert Stent into Plating Cell

Remove the stent from its sterile packaging. Avoid damaging or touching the stent with bare fingers.

Figure 2:
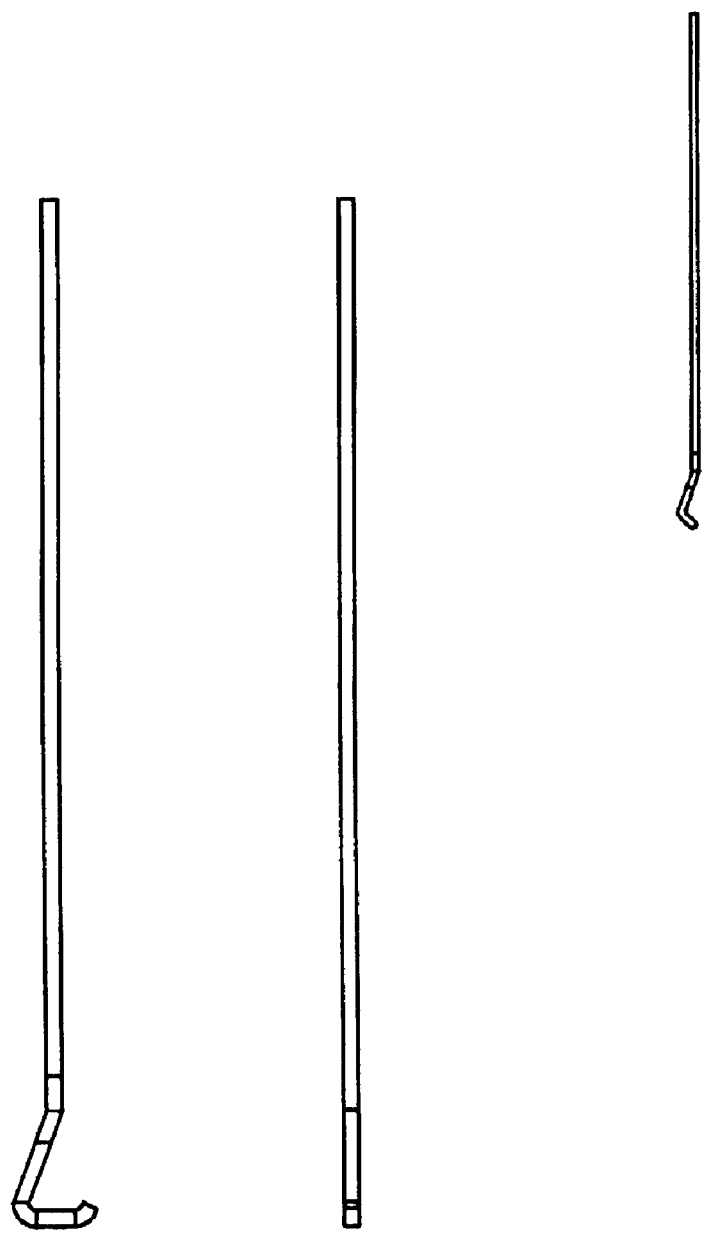
FIG. 2 illustrates various views of a cathode utilized in the plating cell of the preferred embodiment of the present invention.

Mount the stent onto the wire cathode (see FIG. 2) by sliding the wire through the center of the stent. Allow the stent to drop down to the loop at the bottom of the cathode. The stent needs to contact the metal wire for electrical connection in the subsequent steps.

Lower the cathode wire (loop-first) into the burette ensuring that loop is centered in the slot in the bottom locator. (Rotate the wire until the loop drops into the slot).

D. Degrease Stent

Confirm that the stopcock drain valve on the plating cell is closed.

Fill the strike cell with 4 mL of ethanol. Allow the stent to soak for 2 minutes.

Place the "non-radioactive waste" beaker under the plating cell and open the stopcock to drain out the degreasing solution.

Leave the stopcock open and flush deionized water through plating cell to flush liquid from the cell.

Close the stopcock and fill the cell with 4 mL of deionized water. Allow stent to soak for 30 seconds. Drain the cell into the waste beaker and dump beaker into non-radioactive liquid waste collection container.

Rinse the cell with about 3 mL of 1N HCl and immediately drain to prevent dilution of strike reagent during the following step. Proceed immediately to the next step.

E. Anodically Etch Stent

Place top or upper cathode locator (see FIG. 3) over wire end and rest it on edge of cell. Line up spacer slot in top locator with the outer electrode tab. Do not lower the spacer all the way into the burette, i.e. leave it loose.

With the DC power supply off, clip the red (positive) lead to outer electrode tab and the black (negative) lead to the wire cathode at a point above the top locator.

Switch the power supply polarity switch to "Anodic Etch" and proceed immediately to the next step.

Turn on the constant current DC power supply and proceed immediately to the next step.

Using a pipette, transfer the strike electrolyte (label solution) to the strike cell. (There should be sufficient electrolyte to barely cover the stent.) Drop the upper cathode locator into the burette and check position of electrodes and liquid level.

Ensure no electrical shorts exist (zero voltage reading). Adjust the current to the level for the stent being labeled (see Table 3 below). Watch the voltage reading and adjust the cathode if a short occurs (zero volts). When the voltage drops from ~1.2V to ~0.8V (normally ~0.5–1.5 minimum), proceed immediately to the next step.

Switch the polarity reversal switch to "Strike/Plate" and proceed immediately to the next section.

TABLE 3

1.8 mm Diameter Coronary Wave Stent Strike Current

| Stent length (mm) | Strike Current (mA) |
|---|---|
| 9 | 9.2 |
| 12 | 12.2 |
| 16 | 16.3 |
| 19 | 19.4 |
| 26 | 26.5 |
| 32 | 32.6 |

F. Strike $^{188}$Re onto Stent

In the last step above, the polarity reversal switch was set to "Strike/Plate" to initiate the $^{188}$Re strike.

Watch the voltage output and immediately adjust the cathode if a short occurs (the voltage drops to zero).

After 5 minutes, open the stopcock and drain the contents of the reactor burette to radioactive waste collection container.

Immediately shut off the DC power and proceed to the next section.

G. Rinse Stent

Unclip the black (negative) clip lead from the cathode and remove the upper cathode locator from the cell and cathode.

With the waste receiver still in place, rinse cell walls and electrodes with ethanol to flush residual strike bath from the reactor. Close the stopcock. Add 4 mL of ethanol to the reactor, sufficient to cover the stent. Allow the stent to soak for 30 seconds.

Open the stopcock to drain out the rinse solution.

Close the stopcock and empty the waste vial into radioactive liquid waste collection container.

Using protected fingers, carefully (to avoid scraping the coating on the stent) lift the cathode wire with stent out of the plating cell. The stent should be a fairly uniform, reddish, matte copper color.

H. Transfer Stent to Plate Cathode

Grasp the bottom loop of the cathode with 6-inch forceps and invert into a 20 mL glass vial to slide the stent off of the cathode. A second pair of forceps may be required to carefully push the stent off of the cathode.

Once the stent has been removed from the strike cathode, gently insert a tin-plated cathode wire into one end of the stent.

Grasp the bottom loop of the cathode with 6-inch forceps and invert the glass vial so that the stent slides onto the cathode down to the bottom loop.

Grasp the top of the cathode with protected fingers and proceed to the next step.

I. Tin Plate Stent ($^{188}$Re Label Sealing Step)

Lower the cathode wire (loop-first) with stent into the plating cell burette ensuring that the stent does not scrape the sides of tin anode, and that the loop is centered in the slot in the bottom locator. (Rotate the wire until the loop drops into the slot).

Place the top locator over the cathode wire end and rest it on the burette lip. Line up top locator slot with anode tab wire. Do not lower the spacer all the way into the burette at this time.

Attach the black clip (negative) lead to wire-with-stent cathode at a position above the top locator, and the red (positive) clip lead to the anode tab. Check to make sure that the drain valve is closed.

Place a radioactive waste collection beaker under the plating cell.

Turn the plating power supply on. Proceed immediately to the next step.

Use a pipette to transfer the appropriate amount of tin plating solution to the plating cell (Table 2). Shift the top locator to center of the plating cell. Ensure that there is not an electrical short between the electrodes (zero volts). Adjust the cathode if a short occurs.

Immediately adjust current to the prescribed level for the stent being sealed (see Table 4 below). Start timer.

After 2 minutes and 30 seconds, open the plating cell stopcock to drain the plating solution from the reactor to stop the plating process. Proceed immediately to the next steps.

Shut off the DC power to the cell. Unclip the DC power clip leads and remove the upper locator. Leaving the stopcock open, rinse the cell walls and electrodes with a few mL of 60%/40% ethanol/water rinse solution from a wash bottle to flush any remaining tin bath.

Close the stopcock.

TABLE 4

1.8 mm Diameter Coronary Wave Stent Plate Current

| Stent length (mm) | Plate Current (mA) |
|---|---|
| 9 | 3.9 |
| 12 | 5.3 |
| 16 | 7.0 |
| 19 | 8.3 |
| 26 | 11.4 |
| 32 | 14.0 |

If the tin plate anode has not been used for more than 12 hours, it should be conditioned before use. (See "Preconditioning of Tin Plating Cell Anode" below.) Further, inspect the tin plate bath solution to confirm that it is clear and has the color of tea. If any opacity or precipitation is observed, the solution should filtered using a 0.2 μm filter.

J. Rinse Stent

To the plating cell containing the labeled and sealed stent add 4.0 mL of 60%/40% ethanol/water rinse solution. Allow the stent to soak for 30 seconds.

Open the stopcock to drain out the rinse solution into the radioactive waste container.

Empty the waste container into radioactive waste holding container.

Using protected fingers, carefully lift the cathode wire with stent out of the plating cell. It should be a fairly uniform low gloss light-gray color.

K. Transfer Stent to Sterile Tube

Grasp the loop-end of the cathode wire with forceps. Place a sterile 10×75 mm vial into a pig.

Invert the cathode wire so that the stent slides down the wire and into the vial (the stent may need to be gently pushed down the wire with another pair of forceps).

Remove the cathode wire and place it in the solid radioactive waste container unless it is to be re-used within 12 hours.

Option: Fill vial with ethanol/water solution.

Cap the vial.

L. Measure Stent Radioactivity

Place the vial and stent into the dose calibrator carrier using a custom centering fixture (see below) to locate the vial in the center of the carrier.

Lower the carrier into the dose calibrator.

Record the activity measured.

Perform any needed calculations.

M. Storage of Plating Anode (if Cells are Re-used)

To reduce air passivation of the plating anode, it is recommended that when not in use for extended times (such as overnight) the plating cell be filled with sterile water so that the anode coils are submersed.

N. Preconditioning of Tin Plating Cell Anode

The tin anode will passivate (tarnish) quickly in the air. The anode should be preconditioned after fabrication or after greater than 12 hours of idle time prior to being used to plate stents. Preconditioning can be accomplished by plating a cathode wire with tin using the procedure described below.

Insert plating cathode into tin plate cell and center in bottom centering insert groove.

Fill cell with tin sulfate plating solution (about 4 mL).

Insert the top centering spacer and attach clip leads—red to outer electrode and black to center cathode wire.

Set the polarity switch to the "Strike/Plate" position and turn on the power supply.

Adjust current to apply 40 mA current for 10 minutes to the cell.

Drain the cell and turn power off.

Rinse the cell thoroughly with de-ionized water and remove cathode.

The plating anode is now ready for tin plating of stents. The plated cathode can be used as a cathode in the stent tin plate step.

EXAMPLE 2

Stent Compression onto a Catheter Balloon

Stents must be compressed onto a catheter balloon for implantation. The following procedure was designed to reduce technician exposure to Beta radiation and to minimize the potential damage to the tin plating on the stent surface.

Obtain a catheter balloon with the correct outer diameter and length for the stent that is to be mounted.

Remove the catheter balloon from its sterile package. Remove the interior wire and snip off the end loop.

Remove the sheath (if present) from end of balloon.

Fill a catheter balloon pump with 10 mL of de-ionized water and purge excess air.

Attach the catheter balloon pump to the end of catheter using the luer lock fitting.

Pull 1 to 2 psia of vacuum on the catheter balloon.

Insert the end of the catheter balloon into the vial containing the stent.

Gently guide the balloon end into one end of the stent until it is firmly inserted into the stent.

Remove the catheter balloon with the stent from the vial and gently center the stent onto balloon between metal balloon constraints using fine-tipped metal forceps. If the stent is not firmly seated on catheter balloon, exert a small amount of positive pressure to the catheter balloon until stent no longer easily moves. However, do not begin full stent expansion yet.

Replace the interior wire that has had the loop removed.

Insert the catheter balloon and stent into the stent compression tube (see below).

Hold the catheter balloon in place with one hand while using flat-faced pliers to compress the stent onto the balloon.

Move along the stent lengthwise and rotate for even compression. Avoid flattening the stent.

Remove the stent and catheter balloon from the stent compression tube and inspect to confirm that no flaking or peeling has occurred.

Remove the interior wire.

EXAMPLE 3

Stock Solution Preparation

A. Tin Plate Solution

To a 100 mL volumetric flask, add 10.00 mL concentrated sulfuric acid ($H_2SO_4$) followed by 2.10 g of stannous sulfate. Then add 3.000 mL Tinol S Starter B solution followed by 0.075 mL Tinol S Brightener solution. Fill to 100 mL with deionized water.

This solution will oxidize quickly with exposure to air. Lid should be capped tight as quickly as possible after use and the solution should be remade if yellowish color darkens noticeably. Tin oxide also precipitates as the solution ages and this precipitate should not be remixed before use. This will cause tin plate to have a higher granularity. Once significant precipitation has occurred the solution should be remade. Inclusion of a few pieces of granular tin or a coil of tin wire submerged in the reagent will greatly extend its shelf life.

B. Tin Plate Rinse Solution

60%/40% by volume ethanol/water mix.

EXAMPLE 4

Plating Cell Fabrication

In the preferred embodiment described above, two plating cells are required to perform the radiolabeling process. Alternately, however, any suitable number of plating cells could be used, including one plating cell.

According to the preferred embodiment, one plating cell is used for the anodic clean and strike process steps and associated rinses. The other plating cell is used for the plating process step and rinses. The cells are the same except for the anode material.

The materials required to fabricate the two plating cells are provided below in Table 5.

TABLE 5

Materials Required to Fabricate Two Plating Cells

| Material | Quantity Required |
| --- | --- |
| 25 ml burette Pyrex brand Accu-Red burette Class A (Aldrich P/N Z13826-6) | 2 |
| 1 mm wire (316L stainless steel Tungsten Inert Gas (TIG) welding wire) | 15 cm (each cell) |
| 1.6 mm diameter copper wire | 40 cm |
| 1.6 mm diameter tin wire | 40 cm |
| 2 cm diameter PTFE rod | 3.5 cm (each cell) |
| 1 cm diameter PTFE rod | 0.5 cm (each cell) |
| 1.6 mm outer diameter thin wall polyolefin heat shrinkable tubing | 1 cm (each cell) |

The process below can be used to fabricate the two plating cells.

Modify the burette as follows:

Cut burette at 20 mL line and polish edges. Note that if an alternate burette is used, the cut line may need to be adjusted to maintain the distance of the top from the lower cathode locator. This distance is controlled by the requirement for both the cathode wire and the anode tab to extend outside the cell for electrical connections.

Cut the burette outlet tube off approximately 4 cm below the stopcock centerline (above start of taper) and polish edges.

Enlarge the existing outlet hole in PTFE stopcock out to 3.5 mm diameter.

Figure 3:
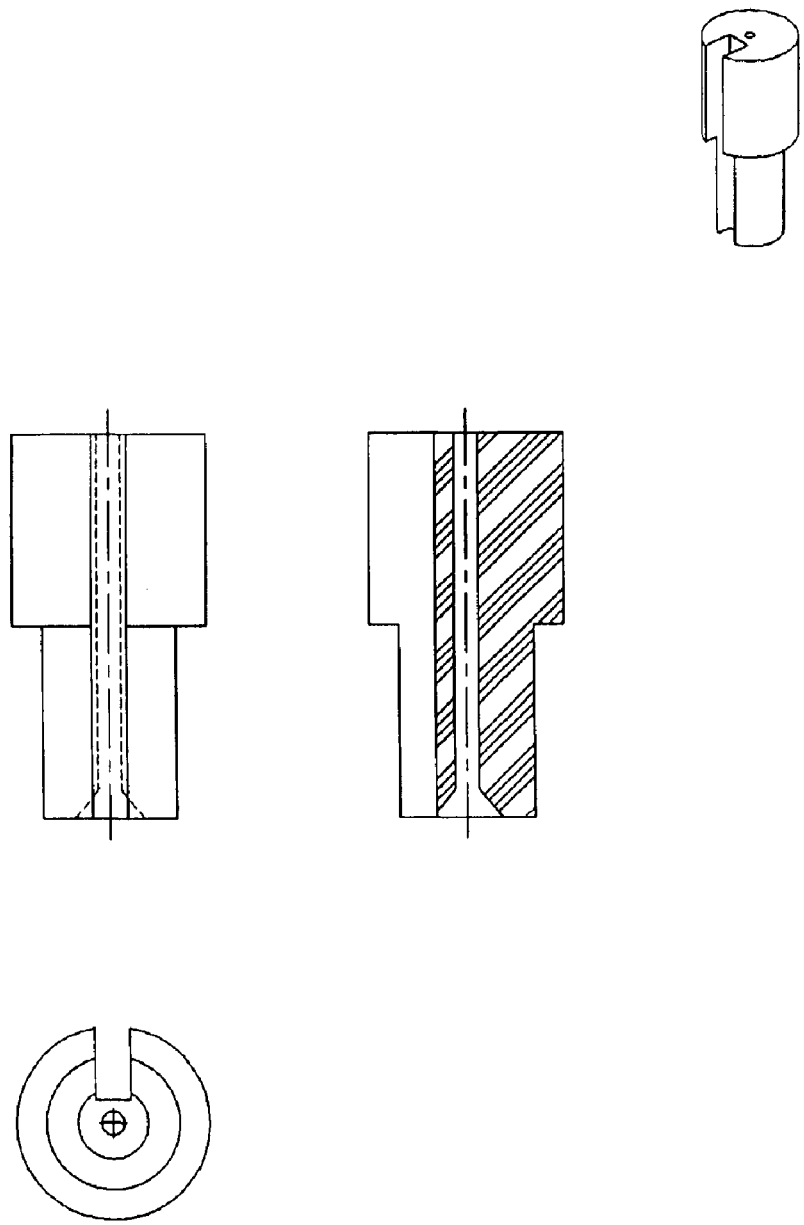
FIG. 3 illustrates various views of an upper cathode locator utilized in a preferred embodiment of the present invention.
Figure 4:
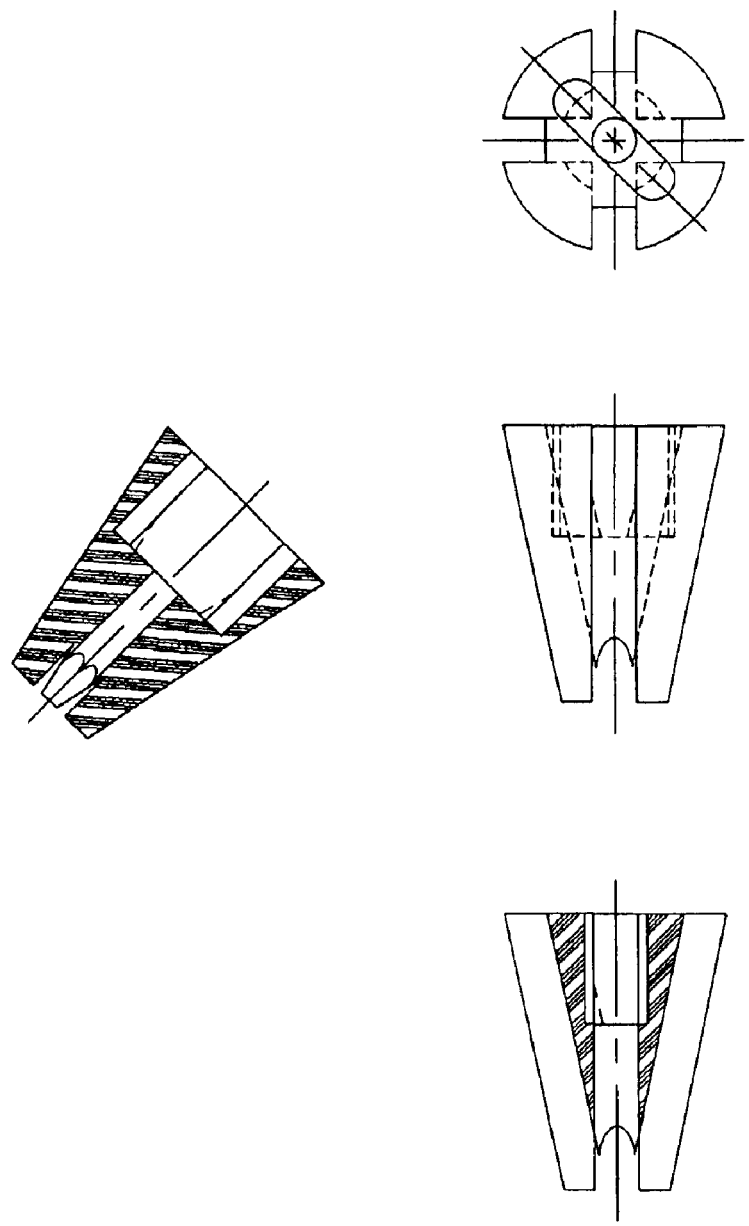
FIG. 4 illustrates various views of a lower cathode locator utilized in a preferred embodiment of the present invention.

Machine the upper and lower cathode locators from PTFE rod (see FIGS. 3 and 4). Fabricate the strike cathodes from stainless steel wire (see FIG. 2) as follows:

Cut wire to 15 cm length.

Form 5 mm diameter bend in one end using needle nose pliers. The cathode wire should be straight enough that a 60 mm long stent can slide freely along its length.

Slip heat-shrink tubing over the formed end of the cathode and shrink in place. Do not exceed the line shown in drawing. Verify that stents placed on the cathode touch the metal at the bottom and not insulation. Trim insulation to expose cathode metal and fit easily into and out of anode coil as necessary.

Fabricate plate cathodes from stainless steel wire (see FIG. 2) as follows:

Follow the preceding instructions for creation of a strike cathode.

Precondition plate cathodes before use by plating tin onto the shaft.

Insert cathode into plate cell and fill with tin sulfate solution

Center cathode and attach clip leads—red on anode, black on cathode

Move polarity switch to "Label/Plate" and switch power to "on"

Adjust current to 40 mA and plate for 2 minutes

Drain, shut off power, rinse cell, and remove cathode.

Fabricate anodes (one copper and one tin) from metal wire (see FIG. 1) as follows:

Cut wire to 40 cm.

Roll into cylinder over around 4.5 mm mandrel with pitch of 3 turns per cm

Condition anode by running plating operation three times using the standard plating solution and a stainless steel cathode without a stent.

Assembly

Drop the lower cathode locator into the burette and then insert the anode. Ensure that no bends are touching and that spacing is about 2 mm and even between loops. Bend the top tab of the anode over the top of the burette for electrical connection.

Stent is mounted on cathode and cathode is inserted into cell and centered in lower locator.

Upper cathode locator is inserted onto cathode wire through center hole and cathode notch lined up with top of anode wire.

Power supply clip leads are connected to anode and cathode and even spacing from top to bottom verified.

EXAMPLE 5

Dose Calibrator Centering Fixture

The dose calibrator is a commercially available item, but the caddy for lowering items into the dose calibrator well for storage should have a fixture that locates the vial containing the stent in the center of the well. The fixture will need to be designed to fit the dose calibrator selected for producing the radiolabeled implantable devices of the present invention. For the preferred embodiment of the present invention, a spacer was fabricated from polycarbonate with an outer diameter that fit into the carrier and a hole formed in the center that was slightly larger than the diameter of the vial. Clearance was left so that the top of the vial could be grasped with forceps.

EXAMPLE 6

Stent Compression Tube

The tube used for compressing the stent onto the catheter balloon is constructed of 5 mm (internal diameter) Tygon flexible tubing. The compression tube is prepared by cutting a piece of flexible Tygon® tubing that is 3 cm longer than the stent to be radiolabeled. The tubing should have a wall thickness of 1.6 mm.

EXAMPLE 7

Plating Power Source Fabrication

The plating power source consists of two power supplies, one for the strike cell and one for the plating cell. Alternately, one power source with two separate sets of leads could be used. The power source for the strike cell includes a switch that reverses polarity at the clip leads so that anodic cleaning and the strike (i.e., labeling) can be performed without physically moving the clip leads.

A. Components 5W, 4A DC power source (2) with digital readout and banana plug compatible outlets Clip leads (red and black, 2 pair)

Banana plugs (red and black)

Electrical toggle switch, double-pole, double-throw (one)

Switch enclosure (one)

5 meters 18 gauge copper wire

B. Anodic Clean/Strike Cell Power Wiring

Attach red and black clip leads to the switch with 60 cm lengths of wire so that red is positive and black is negative in the normal or up position and polarity is reversed when the switch position is changed.

Attach banana plugs to the switch with 60 cm lengths of wire so that red is positive and black is negative in normal or up position.

Mount switch in switch box with normal position (up) labeled as "Strike/Plate" and down as "Anodic Clean."

Plug red banana plug into red power supply socket and black banana into black power supply socket.

C. Plating Cell Power Wiring

Attach a red clip lead and a red banana plug to opposite ends of a one-meter length of wire. Repeat for black clip lead and banana plug.

Plug red banana plug into red power supply socket and black banana into black power supply socket.

Materials and Equipment

The following materials and equipment may be used in conjunction with the above examples.

A. Process Solutions

Ethyl Alcohol, Denatured: HPLC Grade (91% pure)—Aldrich Chemical Co.

Deionized Water, 18.2 Mohm-cm: Sterile, de-ionized water from Millipore Milli-Q Plus System—used for rinse steps and to make up stock strike and tin plate solutions.

Hydrochloric Acid, 2N solution (strike solution): Reagent Grade—Mallinckrodt Baker, Inc.

Hydrochloric Acid, 1N solution (strike and rinse solution): Reagent Grade—Mallinckrodt Baker, Inc.

Sulfuric Acid, concentrated (Tin Plate Solution): A.C.S. Reagent Grade—Mallinckrodt Baker, Inc.

Stannous Sulfate (Tin Plate Solution): 95+% pure—Aldrich Chemical Company

Tinol S Starter B (Tin Plate Solution): Maclee Chemical Co.

Tinol S Brightener B (Tin Plate Solution): Maclee Chemical Co.

B. Equipment

DC Power Supply: Hewlett Packard Harrison 6290A DC Power Supply

Dose Calibrator: Syncor CRC-7 Radioisotope Calibrator

Radiation Shielding: 3-inch thick leaded glass standing shield with a ½-inch thick acrylic sheet (attached to the side nearest the plating cells).

While the invention has been described above in terms of radiolabeling an implantable device with a radioactive isotope of Re, the present invention broadly contemplates the use of electroplatable metal radioactive isotopes as radiolabeling agents for implantable devices. For example, in addition to Re, radioactive isotopes of the following elements may be suitable for and are contemplated by the present invention as radiolabeling agents: Be, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Te, Hf, Ta, W, Os, Ir, Pt, Au, Hg, Tl, Pb, Bi, Po, At, Th, Pa, U, Np, Pu, Am, Cm, Bk, Cf, Es, Fm, Md, No and Lr.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

What is claimed is:

1. A radioactive implantable device comprising:
    a base;
    a first layer comprising Cu and a radioactive isotope on the base; and
    a second layer comprising Sn on the first layer.

2. The radioactive implantable device of claim 1 wherein the base comprises stainless steel.

3. The radioactive implantable device of claim 1 wherein the radioactive isotope comprises a radioisotope of Re.

4. The radioactive implantable device of claim 3 wherein the radioactive isotope of Re comprises $^{188}$Re or $^{186}$Re.

5. A process of producing a radioactive implantable device according to claim 1, the process comprising:
   depositing a first layer comprising Cu and a radioactive isotope on a base; and
   depositing a second layer comprising Sn on the first layer.

6. The process of claim 5 wherein the isotope comprises a radioisotope of Re.

7. The process of claim 6 wherein the radioactive isotope of Re comprises $^{188}$Re or $^{186}$Re.

8. The process of claim 5 wherein the base comprises stainless steel.

9. The process of claim 8, futher comprising the step of removing $Cr_2O_3$ from the base prior to depositing the first layer thereon.

10. The process of claim 9 wherein the removal step comprises electroetching the base.

11. The process of claim 10 wherein the electroecthing step comprises placing the base in a solution comprising HCl and Re.

12. The process of claim 10 wherein the electroecthing step is conducted on the base until a voltage drop is observed.

13. The process of claim 9 wherein the removal step comprises immersing the base in an acid solution.

14. The process of claim 13 wherein the acid solution comprises HCl.

15. The process of claim 14 wherein the acid solution is heated to approximately 100° C.

16. The process of claim 5, futher comprising the step of rinsing the base prior to depositing the first layer thereon.

17. The process of claim 16 wherein the rinsing step comprises immersing the base in ethanol or water.

18. The process of claim 5, further comprising degreasing the base, sterilizing the base and/or minimizing microbiological activity on the base.

19. The process of claim 5 wherein the first layer is deposited on the base by electrochemical deposition comprising a cathode and an anode connected to a voltage source and immersed in a solution.

20. The process of claim 19 wherein the cathode comprises the base, the anode comprises Cu and the solution comprises a radioactive isotope in HCl.

21. The process of claim 20 wherein the radioactive isotope comprises a radioactive isotope of Re.

22. The process of claim 21 wherein the radioactive isotope of Re comprises $^{188}$Re or $^{186}$Re.

23. The process of claim 21 wherein $Cu^{2+}$ is release from the anode into the solution and then co-deposited withe the radioactive isotope of Re onto the base.

24. The process of claim 19 wherein the length of the anode is substantially equal to the length of the cathode.

25. The process of claim 19 wherein the anode substantially extends along the length of the cathode.

26. The process of claim 25 wherein the anode is substantially disposed around the circumference of the cathode.

27. The process of claim 26 wherein the anode comprises a plurality of turns.

28. The process of claim 27 wherein the anode comprises two ends sections and a middle section, and further wherein the turns in the middle section are more tightly wound than the turns in the end sections.

29. The process of claim 26 wherein the anode comprises a cylindrical mesh.

30. The process of claim 26 wherein the anode comprises a solid cylindrical sheet.

31. The process of claim 25 wherein the anode comprises a wire.

32. The process of claim 19 wherein the anode does not substantially extend along the length of the cathode.

33. The process of claim 19 wherein current level is reduced from a first level to a second level during the electrochemical deposition.

34. The process of claim 19 comprising electropolishing the surface finish of the first layer.

35. The process of claim 19 wherein the current direction is switched from a first direction to a second direction during the electrochemical deposition.

36. The process of claim 35 wherein the switch in current direction is maintained for a period of time during the electrochemical deposition.

37. The process of claim 35 comprising electropolishing the surface finish of the first layer.

38. The process of claim 19 wherein the duration of the electrochemical deposition is adjusted to customize the radioactivity level of the implantable device and/or to compensate for the radioactive decay of the radiolabeling solubion.

39. The process of claim 19 wherein the current is adjusted during the electrochemical deposition to customize the radioactivity level of the implantable device and/or to compensate for the radioactive decay of the radiolabeling solution.

40. The process of claim 19 wherein the current and duration of the electrochemical deposition is adjusted to customize the radioactivity level of the implantable device and/or to compensate for the radioactive decay of the radiolabeling solubion.

41. The process of claim 19 wherein gas is released from the solution during the electrochemical deposition.

42. The process of claim 41 wherein the gas is $O_2$ or $H_2$ or any combination of these gases.

43. The process of claim 19 further comprising mixing the solution.

44. The process of claim 5 wherein the second layer is on the first layer by electrochemical deposition comprising a cathode and an anode connected to a voltage source and immersed in a solution.

45. The process of claim 5, further comprising:
   rinsing the base comprising the first layer deposited thereon prior to depositing the second layer thereon.

46. The process of claim 5 further comprising removing a desired amount of radioactivity from the radioactive implantable device.

47. The process of claim 46 wherein the rinsing step comprises immersing the base in ethanol or water.

48. The process of claim 5 wherein the steps of depositing the first and second layers occurs by electrochemical deposition.

49. The process of claim 48 wherein the electrochemical deposition of the first and second layers occurs in a single electrochemical cell.

50. The process of claim 48 wherein the electrochemical deposition of the first layer occurs in a first electrochemical cell and the electrochemical deposition of the second layer occurs in a second electrochemical cell.

51. The radioactive implantable device of claim 1 wherein the radioactive isotope is selected from the group consisting of radioactive isotopes of Re, Be, Sc, Ti, V, Cr, Mn, Fe, Co, Ni, Cu, Zn, Ga, Ge, As, Y, Zr, Nb, Mo, To, Ru, Rh, Pd, Ag, Cd, In, Sn, Sb, Te, Hf, Ta, W, Os, Ir, Pt, Au, Hg, Tl, Pb, Bi, Po, At, Th, Pa, U, Np, Pu, Am, Cm, Bk, Cf, Es, Fm, Md, No and Lr.

* * * * *

UNITED STATES PATENT AND TRADEMARK OFFICE
CERTIFICATE OF CORRECTION

PATENT NO. : 6,855,103 B2
DATED : February 15, 2005
INVENTOR(S) : Ludger Dinkelborg et al.

It is certified that error appears in the above-identified patent and that said Letters Patent is hereby corrected as shown below:

Title page,
Item [75], Inventors, add the following:
-- Bruce F. Monzyk, Delaware (OH); Stephen C. Schmitt, Dublin (OH); Chad M. Cucksey, Columbus (OH); Derek Campbell, Sebastopol (CA). --

Column 14,
Line 61, reads "radioactive is tope" should read -- radioactive isotope --.

Column 15,
Line 8, reads "wherein the isotope" should read -- wherein the radioactive isotope --.
Line 14, reads "futher comprising" should read -- further comprising --.
Lines 19 and 22, reads "electroecthing" should read -- electroetching --.
Line 47, reads "is release" should read -- is released --.
Line 48, reads "co-deposited withe" should read -- co-deposited with --.

Column 16,
Line 37, reads "layer is on" should read -- layer is deposited on --.
Line 61, reads "Nb, Mo, To," should read -- Nb, Mo, Tc, --.

Signed and Sealed this

Fourteenth Day of June, 2005

JON W. DUDAS
*Director of the United States Patent and Trademark Office*